(12) United States Patent
Seo et al.

(10) Patent No.: US 12,346,639 B2
(45) Date of Patent: Jul. 1, 2025

(54) ELECTRONIC APPARATUS FOR PROVIDING COLLABORATIVE SERVICE BETWEEN OPERATOR AND USER FOR DESIGN OF PATIENT-CUSTOMIZED BODY MODEL OR MEDICAL DEVICE AND METHOD THEREOF

(71) Applicant: SeeAnn Solution Co., Ltd., Incheon (KR)

(72) Inventors: Anna Seo, Incheon (KR); Youngjin Jeong, Incheon (KR); Hakjong Noh, Incheon (KR)

(73) Assignee: SeeAnn Solution Co., Ltd., Incheon (KR)

( * ) Notice: Subject to any disclaimer, the term of this patent is extended or adjusted under 35 U.S.C. 154(b) by 0 days.

(21) Appl. No.: 18/516,273

(22) Filed: Nov. 21, 2023

(65) Prior Publication Data
US 2024/0202395 A1    Jun. 20, 2024

(30) Foreign Application Priority Data
Dec. 15, 2022   (KR) .................. 10-2022-0176361

(51) Int. Cl.
*G06F 30/20* (2020.01)
(52) U.S. Cl.
CPC .................... *G06F 30/20* (2020.01)
(58) Field of Classification Search
CPC ........................................... G06F 30/20
See application file for complete search history.

(56) References Cited

U.S. PATENT DOCUMENTS

| 11,304,760 | B1* | 4/2022 | Roh | A61B 34/30 |
| 2017/0249440 | A1* | 8/2017 | Lang | B33Y 50/02 |
| 2022/0047402 | A1* | 2/2022 | Casey | A61B 90/98 |

FOREIGN PATENT DOCUMENTS

| KR | 10-2011-0087220 A | 8/2011 |
| KR | 10-2020-0117118 A | 10/2020 |
| KR | 10-2021-0001455 A | 1/2021 |
| KR | 10-2207026 B1 | 1/2021 |

OTHER PUBLICATIONS

An Office Action mailed by the Korean Intellectual Property Office on Jan. 18, 2024, which corresponds to Korean Patent Application No. 10-2022-0176361 and is related to U.S. Appl. No. 18/516,273.

* cited by examiner

*Primary Examiner* — Chuen-Meei Gan
(74) *Attorney, Agent, or Firm* — Studebaker Brackett PLLC

(57) ABSTRACT

Provided is a method of providing a collaborative service between an operator and a user for design of a patient-customized body model or a patient-customized medical device in an electronic apparatus, the method including: acquiring one or more pieces of suggested information related to provision of the patient-customized body model or the patient-customized medical device; providing the one or more pieces of suggested information to a user; receiving response information regarding the one or more pieces of suggested information from the user; and upon receiving a modification request for at least a part of the one or more pieces of suggested information as the response information, initiating a process for modifying the at least a part of the one or more pieces of suggested information.

9 Claims, 18 Drawing Sheets

TEXT MEMO

GENERATE TEXT MEMO

NEW : GENERATE NEW MEMO
SORT : SORT MEMO
HIDE : HIDE MEMO

400

SURGERY PREPARATION →
- EQUIP YOURSELF WITH SURGICAL TOOLS (VIEW MORE)
- WEAR SURGICAL GOWN (VIEW MORE)
- PREPARE FOR IMPLANT (VIEW MORE)
410

SURGERY START →
- ANESTHETIZE PATIENT (VIEW MORE)
- DISINFECT SURGICAL SITE (VIEW MORE)
- INCISE SURGICAL SITE (VIEW MORE)
420

IMPLANT INSERTION →
INSERT IMPLANT AT LOCATION INDICATED IN PHOTO BELOW (VIEW MORE)
430

ELECTRONIC APPARATUS FOR PROVIDING COLLABORATIVE SERVICE BETWEEN OPERATOR AND USER FOR DESIGN OF PATIENT-CUSTOMIZED BODY MODEL OR MEDICAL DEVICE AND METHOD THEREOF

CROSS-REFERENCE TO RELATED APPLICATION

This application claims priority to and the benefit of Korean Patent Application No. 10-2022-0176361, filed on Dec. 15, 2022, the disclosure of which is incorporated herein by reference in its entirety.

BACKGROUND

1. Field of the Invention

The disclosure relates to an electronic apparatus for providing a collaborative service between an operator and a user in three-dimensional (3D) modeling for the design of a patient-customized body model or medical device in relation to the provision of a medical service, and a method thereof.

2. Discussion of Related Art

As medical technology advances, medical services are progressively diversifying and more specialized. Additionally, with the development of electronic technology, there is an increasing trend to provide medical services using electronic technology. The use of electronic technology may include various acts of utilization, such as of not only applying electronic technology to devices for direct medical treatment, but also providing remote medical services or selling various items on an e-commerce web page.

However, since medical services deal with human lives and health, it is required to carefully consider various factors related to each service, such as physical characteristics of individual patents, and determine details of the service provided.

As relevant arts, reference may be made to Korean Patent Publication No. 10-2020-0117118A or Korean Patent Publication No. 10-2011-0087220A.

SUMMARY OF THE INVENTION

The present invention is directed to providing an electronic apparatus for providing a collaborative service between an operator and a user in relation to three-dimensional (3D) modeling for designing or producing a patient-customized body model or a patent-customized medical device in relation to provision of a medical service.

The technical challenges that this embodiment aims to achieve are not limited to the technical challenges described above, and other technical challenges may be inferred from the following embodiments.

According to an aspect of the present invention, there is provided a method of providing a collaborative service between an operator and a user for design of a patient-customized body model or a patient-customized medical device in an electronic apparatus, the method including: acquiring one or more pieces of suggested information related to provision of the patient-customized body model or the patient-customized medical device; providing the one or more pieces of suggested information to a user; receiving response information regarding the one or more pieces of suggested information from the user; and upon receiving a modification request for at least a part of the one or more pieces of suggested information as the response information, initiating a process for modifying the at least a part of the one or more pieces of suggested information.

The acquiring of the one or more pieces of suggested information may include generating at least a part of the one or more pieces of suggested information based on information related to a target patient.

The one or more pieces of suggested information may include at least one piece of information selected from: 3D modeling information about a body part of a target patient; 3D modeling information about a medical device customized to a body part of a target patient; information about a simulation result of applying the medical device to a body part of a target patient; specific guidance information for applying the medical device to a body part of a target patient; information for providing a 3D modeling production function for a patient-customized medical device; and matching information obtained by overlaying medical image data of a target patient on 3D modeling information about a body part of a target patient or on a 3D modeling image of a patient-customized medical device.

The response information may include: 3D modeling information obtained by manipulating shifting, zooming-in, zooming-out, rotating, or twisting on at least a part of suggested information of the operator on XYZ axes; or 3D modeling information of all or some of groups of 3D modeling elements included in the suggested information, or image information obtained by manipulating the 3D modeling information about all or some of groups of 3D modeling elements included in the suggested information.

The response information may include a voice chat, a text chat, a text memo, or an image memo that requests modification of at least a part of suggested information of an operator, or content of at least a part of suggested information of an operator that is directly deleted or changed by a user.

The initiating of the process for modifying the at least a part of the one or more pieces of suggested information may further include providing a function for transmitting and receiving information between the user and the operator.

The function for transmitting and receiving the information may include at least one of a function for providing a first interface to the user and a function for providing a second interface to the operator, and the electronic apparatus may reflect at least a part of an input of the operator in the first interface in real time and reflects at least a part of an input of the user in the second interface in real time.

The method may further include grouping the one or more pieces of suggested information and the response information and storing the one or more pieces of suggested information and the response information, which are grouped, in a database.

The method may further include acquiring feedback information related to the acquiring of the one or more pieces of suggested information based on information stored in the database.

The method may further include: acquiring result information of providing a medical service using the patient-customized body model or medical service; and acquiring feedback information related to the acquiring of the one or more pieces of suggested information based on the result information.

The patient-customized medical device may include an implant, a graft material, a surgery guidance, or an orthosis, and the one or more pieces of suggested information may include information for suggesting one or more of: a shape, a material, a color, a transparency, a size, a weight, a price, a manufacturing deadline, an application location, an angle, a depth, and a specific producing operation of 3D modeling of the implant, the graft material, the surgery guidance, or the orthosis.

The user may be a medical professional.

According to an aspect of the present invention, there is provided a non-transitory computer-readable recording medium on which a program for executing the method is recorded, and which is readable by a computer.

According to an aspect of the present invention, there is provided an electronic apparatus for providing a collaborative service between an operator and a user for design of a patient-customized body model or a patient-customized medical device, the electronic apparatus including a transceiver, a memory in which instructions are stored, and a processor, wherein the processor is configured to, in connection with the transceiver and the memory, acquire one or more pieces of suggested information related to provision of a medical service; provide the one or more pieces of suggested information to a user; receive response information regarding the one or more pieces of suggested information from the user; and upon receiving a modification request for at least a part of the one or more pieces of suggested information as the response information, initiate a process for modifying the at least a part of the one or more pieces of suggested information.

Specific details of other embodiments are included in the detailed description and drawings.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
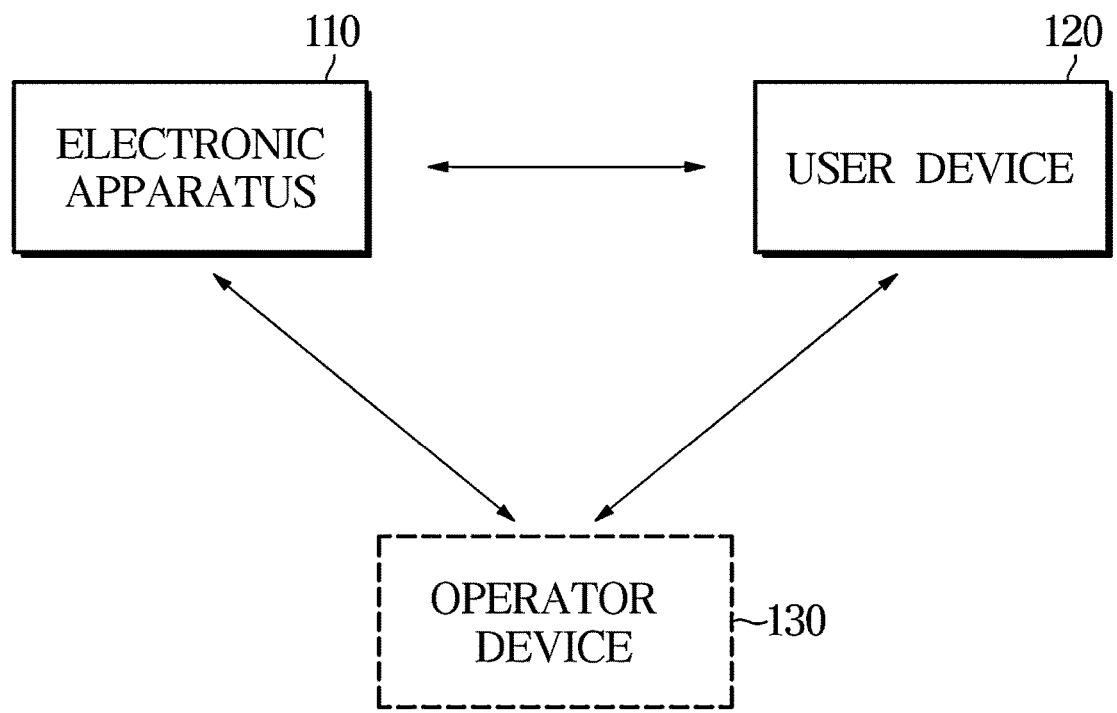
FIG. 1 is a schematic block diagram illustrating a system for providing a collaborative service between an operator and a user in 3D modeling and design for designing or producing a patient-customized body model or a patient-customized medical device according to an embodiment.

Although terms used herein are selected from among general terms that are currently and widely used in consideration of functions in the exemplary embodiments, these may be changed according to intentions or customs of those skilled in the art or the advent of new technology. However, when a specified term is defined and used in an arbitrary sense, a meaning of the term will be described in the specification in detail. Accordingly, the terms used herein are not to be defined as simple names of the components but should be defined based on the actual meaning of the terms and the whole context throughout the present specification.

Throughout the specification, the term "comprises" or "includes" and/or "comprising" or "including" means that one or more other components may not be further excluded unless context dictates otherwise. In the specification, the term "part" or "module" refers to a unit for processing at least one function or operation that may be implemented in hardware, software, or a combination thereof.

As used herein, expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

Meanwhile, a "terminal" described below may be implemented as a computer or a portable terminal capable of connecting to a server or another terminal through a network. Here, the computer may include, for example, a notebook computer, a desktop computer, a laptop PC, and the like, each of which is equipped with a WEB Browser. The portable terminal is a wireless communication device, and may include: all types of handheld devices based on wireless communication, such as a communication-based terminal, e.g., an international mobile telecommunication (IMT), a code division multiple access (CDMA), a w-code division multiple access (W-CDMA), a long term evolution (LTE), and the like, a smart phone, and a table PC.

Although embodiments of the present disclosure will be described in detail with reference to the accompanying drawings in order to enable those skilled in the art to easily practice the disclosure, the present disclosure may be embodied in many different forms and should not be construed as being limited to the embodiments set forth herein.

Hereinafter, embodiments of the present invention will be described in detail with reference to the attached drawings.

In the description of the embodiments, the detailed description of related known functions or constructions will be omitted herein to avoid making the subject matter of the present disclosure unclear.

In the accompanying drawings, sizes of elements may be exaggerated, reduced or schematically illustrated for the sake of convenience in description, and may not reflect actual shapes of each element. In addition, the same drawing reference numerals will be understood to refer to the same elements, features, and structures.

The advantages and features of the present invention and ways of achieving them will become readily apparent with reference to descriptions of the following detailed embodiments in conjunction with the accompanying drawings. However, the present invention is not limited to such embodiments and may be embodied in various forms. The embodiments to be described below are provided only to complete the disclosure of the present invention and assist those of ordinary skill in the art in fully understanding the scope of the present invention, and the scope of the present invention is defined only by the appended claims. In connection with assigning reference numerals to elements in the drawings, the same reference numerals are used for designating the same elements throughout the specification In this case, the combinations of blocks and flowchart illustrations in the process flow charts may be performed by computer program instructions. These computer program instructions may be loaded into a processor of a general purpose computer, special purpose computer, or other programmable data processing equipment so that the instructions, which may be executed by a processor of a computer or other programmable data processing equipment may generate means for performing the functions described in block(s) of the flowchart. These computer program instructions may also be stored in a computer usable or computer readable memory capable of directing a computer or other programmable data processing apparatus to implement the functionality in a particular manner so that instructions stored in the computer usable or computer readable memory may also produce a manufacturing item containing instruction means for performing the functions described in block(s) of the flowcharts. Computer program instructions may also be loaded into a computer or other programmable data processing equipment so that a series of operating steps are performed on the computer or other programmable data processing equipment to generate a computer-executable process and execute the computer or other programmable data processing equipment, providing steps for executing the functions described in block(s) of the flow charts.

Also, each block may represent a module, segment, or portion of code that includes one or more executable instructions for executing the specified logical function (s). It should also be noted that in some alternative embodiments, the functions mentioned in blocks may occur out of order. For example, two blocks shown in succession may be performed substantially concurrently, or the blocks may sometimes be performed in reverse order according to the corresponding function.

FIG. 1 is a schematic block diagram illustrating a system for providing a collaborative service between a user and an operator in 3D modeling for designing or producing a patient-customized body model or a patient-customized medical device in relation to a medical service according to an embodiment.

According to various embodiments, a system 100 for providing a collaborative service may include an electronic apparatus 110 and a user device 120, and may further include an operator device 130 according to embodiments. According to embodiments, the system 100 for providing a collaborative service may further include a network for supporting information transmission and reception between at least a part of the electronic apparatus 110, the user device 120, and the operator device 130.

A medical service refers to all activities performed by medical professionals to protect and promote the health of users.

According to an embodiment, the medical service may include a service using a body organ model, a medical device, a body orthosis, and the like individually user-customized and produced using 3D modeling technology. For example, the medical service may refer to a service of providing a three-dimensional (3D) simulation model that reflects the shape and condition of a user's body part that is subject to various treatments, such as procedures, surgeries, and the like, a service of reconstructing or treating a patient's body part that is damaged or deformed due to various factors, such as a birth condition, a disease, a tumor, a personal injury, a failed previous surgery, and the like, or a service of providing an orthosis to assist a body part that is damaged or deformed, but it is not limited thereto.

According to an embodiment, the patient-customized body model may correspond to a targeted body part of a patent and include a model embodying an abnormal condition in a body part that is damaged or deformed due to various causes, for example, a model of a heart valve on which calcium deposits that requires a surgery or a model of a heart including the heart valve, in which the model may be provided online or produced as a physical object, but it is not limited to.

According to an embodiment, the patient-customized medical device may be a graft material or an implant that may be specifically inserted into a body part having abnormal conditions such as damage, deformation or the like, for example: an orthopedic implant for fixing a bone fracture site; or a surgery guidance for a transplantation surgery of the graft material or implant described above, including a guidance for a shoulder joint replacement surgery, such as a center-pin, a base plate, a screw, and the like or a guidance for a mandibular replacement surgery due to an oral cancer, such as a mandibular support or a cutting guidance for cutting a mandible or other skeletal parts to be transplanted to the mandible, but it is not limited thereto.

According to an embodiment, the patient-customized medical device may correspond to a body part of a patient that is damaged or deformed, and may include, for example, an orthosis for assisting a bent finger or toe, but it is not limited thereto.

The electronic apparatus 110, the user device 120, and the operator device 130 may each include a transceiver, a memory, and a processor. In addition, each of the electronic apparatus 110, the user device 120, and the operator device 130 refers to a unit that processes at least one function or operation, and may be implemented as hardware, software, or a combination of hardware and software. Meanwhile, throughout the embodiment, the electronic apparatus 110, the user device 120, and the operator device 130 are each referred to as separate devices or servers, but they may be structures divided based on a logical aspect, and at least a part of the electronic apparatus 110, the user device 120, and the operator device 130 may be implemented by a function separated from a single device or server.

According to an embodiment, the electronic apparatus 110, the user device 120, and the operator device 130 may include a plurality of computer systems or computer software implemented on a network server. For example, at least a part of the electronic apparatus 110, the user device 120, and the operator device 130 may refer to a computer system and computer software that are connected to a lower level device that may communicate with other network servers through a computer network, such as an intranet or the Internet, and receive a request for task performance, perform the task, and provide a result of performing the task. In addition, at least a part of the electronic apparatus 110, the user device 120, and the operator device 130 may be understood as a broad concept that includes a series of application programs that may operate on a network server and various databases built inside or on other connected nodes. For example, at least a part of the electronic apparatus 110, the user device 120, and the operator device 130 may be implemented using various network server programs provided depending on the operating system, such as DOS, Windows, Linux, UNIX, or MacOS.

The electronic apparatus 110 is a device that configures various types of information and provides the information. The electronic apparatus 110 may provide the configured information in the form of a web page, an application screen, or the like. The electronic apparatus 110 may be a device serving to provide a user and an operator with information related to the provision of a medical service and various types information.

The electronic apparatus 110 acquires one or more pieces of suggested information related to the provision of a patient-customized body model or medical device, and provides the acquired one or more pieces of suggested information to the user. The electronic apparatus 110 may generate at least a part of the one or more pieces of suggested information, and may receive at least a part of the one or more pieces of suggested information from an operator. In addition, the electronic apparatus 110 may acquire suggested information according to other various embodiments.

The electronic apparatus 110 receives response information regarding the one or more pieces of suggested information from the user. The received response information may include various types of information, such as an approval of the suggested information, a rejection of the suggested information, and a request for modification of the suggested information. In addition, when there are rules established regarding an interpretation of cases having no response to a suggestion (for example, that content of suggested information is implicitly determined to have been approved in the absence of a separate response), no response is considered an implied response, in which case, the understanding and interpretation are expanded and considered within the scope of the disclosure.

When the response information includes a modification request related to at least a part of the one or more pieces of suggested information, the electronic apparatus 110 initiates a process for modifying the at least a part of the one or more pieces of suggested information. In this regard, the electronic apparatus 110 may request the operator to modify the at least a part of the one or more pieces of suggested information, may provide a function for transmitting and receiving information between the user and the operator, and additionally, various embodiments may be present in relation to initiating a process for modifying the suggested information.

Further details regarding the operation of the electronic apparatus 110 are described below with reference to FIGS. 2 to 12 and FIG. 15.

A user is an entity that has requested design or production of a patient-customized body model or medical device, and may include various entities related to the provision of medical services using the patient-customized body model or medical device. As an example, the user may include a person who provides medical services and may, for example, be a medical professional. As another example, the user may include a manager who manages and supervise whether there are any problems with the provision of medical services, but it is not limited thereto. In addition, the user according to the present disclosure is not limited to those who provide medical services, and also it should be understood that the disclosure may include an embodiment in which the user makes a confirmation, and then the medical service is finally provided by the electronic apparatus 110 or by the operator.

The user device 120 is a device manipulated and managed by the user. The user device 120 may receive a user input from a user or information from the electronic apparatus 110, and may perform an operation corresponding to the user input or the information. For example, the user device 120 may receive one or more pieces of suggested information from the electronic apparatus 110 and provide the one or more pieces of suggested information to the user. The user device 120 may provide the information received from the electronic apparatus 110 as it is, or may further process the information (for example, convert the information received from the electronic apparatus 110 such that the information is output on an output device, such as a screen or speaker), and provide the processed information. According to embodiments, the user device 120 may further perform various operations, such as receiving a response, such as a modification request from the user, and providing the response to the electronic apparatus 110.

Further details regarding the operation of the user device 120 are described below in FIGS. 12, 13, 14, 15, and 16.

The operator may include an entity that transmits at least a part of the one or more pieces of suggested information to the electronic apparatus 110, or transmits information that is the basis for generating at least a part of the one or more pieces of suggested information to the electronic apparatus 110 (in which case, the suggested information may be finally generated in the electronic apparatus 110). As an example, the operator may include a 3D modeler that three-dimensionally models a medical device or body model, which is to be applied to or inserted into a patient, and transmits the result.

The operator may include but may not be limited to a natural person, and may include comprehensive entities, such as companies related to the provision of medical services. However, for convenience of description, an embodiment in which the operator is a natural person is described, and the following description may be applied to various types of operators.

The operator device 130 is a device manipulated and managed by the operator. The operator device 130 may receive a user input from the operator and the like or information from the electronic apparatus 110 and the like and perform operations corresponding to the user input or the information. For example, the operator device 130 may receive basic information, such as information related to a target patient, from the electronic apparatus 110 and the user device 120, and provide the received basic information to the operator. The operator device 130 may provide the received information as it is, or may additionally process the received information (for example, convert the received information such that the information may be output on an output device, such as a screen or speaker) and provide the processed information. In addition, the operator device 130 may receive an input related to the one or more pieces of suggested information from the operator and provide the received input related to the one or more pieces of suggested information to the electronic apparatus 110, and may further perform various operations, such as transmitting and receiving various types of information related to a modification process.

Further details regarding the operation of the operator device 130 are described below in FIGS. 3 to 14 and the like.

Figure 20A:
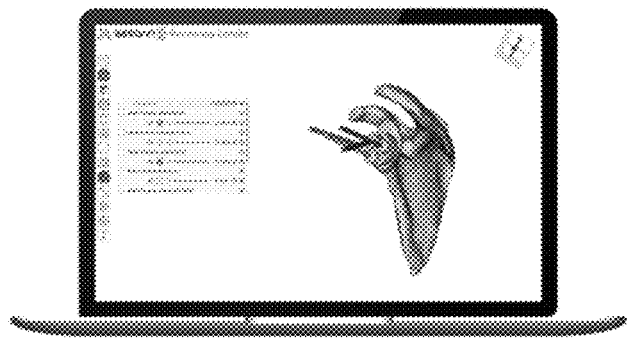
FIGS. 20A, 20B, and 20C are exemplary diagrams illustrating a user device and an operator device according to an embodiment.
Figure 20B:
Figure 20C:

The user device 120 and the operator device 130 may include a computer device, a mobile communication terminal, a server, and the like. The user device 120 and the operator device 130 may include or be connected to an input device, such as a touch pad, a mouse, or a keyboard for receiving a user input. In addition, the user device 120 and the operator device 130 may include, or be connected to an output device, such as a screen, a speaker, or an interface device for providing information to the user. Furthermore, the input device and the output device of the user device 120 or the operator device 130 may be integrated with each other as one part or may be associated with each other. For example, an interface for receiving a user input may be displayed on the user device 120 or the operator device 130. The user device 120 and the operator device 130 may be provided using various terminals, for example, a computer as shown in FIG. 20A, a tablet PC as shown in FIG. 20B, a mobile phone as shown in FIG. 20C, and the like.

A method of performing a series of operations for providing a collaborative service between a user and an operator according to various embodiments may be implemented by a single physical device, or may be implemented by a plurality of physical devices that are organically combined to each other. For example, some components included in the system 100 for providing a collaborative service may be implemented by one physical device, and some other components may be implemented by another physical device. For example, the one physical device may be implemented as a part of the electronic apparatus 110, and the other physical device may be implemented as a part of the user device 120 or a part of another external device. In some cases, components included in the system 100 for providing a collaborative service may be distributed and placed in different physical devices, and the distributed components may be organically combined to perform the functions and operations of the system 100 for providing a medical service. For example, the electronic apparatus 110 in the present specification may include at least one sub-device, and some operations described as being performed by the electronic apparatus 110 may be performed by a first sub-device, and some other operations may be performed by a second sub-device.

Figure 2:
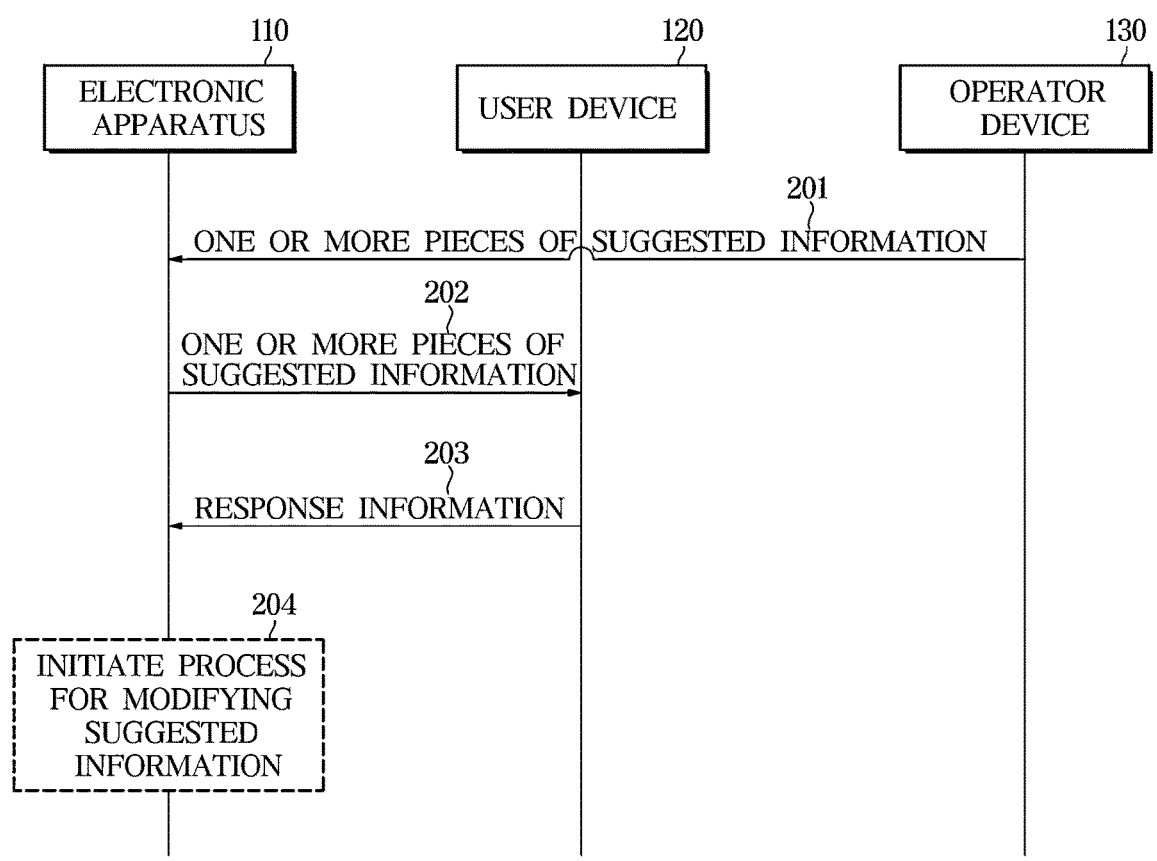
FIG. 2 is an operation flowchart for describing an operation of an electronic apparatus in a system for providing a collaborative service according to an embodiment.

FIG. 2 is an operation flowchart for describing an operation of an electronic apparatus in a system for providing a collaborative service according to an embodiment.

Referring to FIG. 2, in relation to the provision of a medical service, one or more pieces of suggested information regarding 3D modeling of a patient-customized body model or a patient-customized medical device are acquired (201). The one or more pieces of suggested information may be received from the operator device 130. However, the scope of the present disclosure is not limited to receiving the one or more pieces of suggested information from the operator device 130, and according to embodiments, at least a part of the one or more pieces of suggested information may be received from other external devices, or the electronic apparatus 110 may directly generate at least a part of the one or more pieces of suggested information, and also other various embodiments may be present.

As a more specific example, the electronic apparatus 110 according to an embodiment may generate at least a part of the one or more pieces of suggested information based on information related to a target patient. The information related to the target patient may include various types of information, such as the patient's physical condition, the type of disease of the patient, the patient's purpose of receiving a medical service, the patient's medical image data, and the like. According to embodiments, in addition to the information related to the target patient, the electronic apparatus 110 may further generate one or more pieces of suggested information by further considering various types of foundational information, such as the type of equipment owned by the user or the overall medical infrastructure of the region in which the user and the patient are located.

According to an embodiment, the electronic apparatus 110 may receive a request for designing or producing a patient-customized body model or a patient-customized medical device, and in response to the reception of the request, perform operation 201. For example, the electronic apparatus 110 may receive an order for the design or production of a patient-customized body model or medical device from a consumer (a user but not limited thereto, and including various entities, such as a target patient) and accordingly, may acquire one or more pieces of suggested information. In this case, information about the order for the design or production of the patient-customized body model or medical device may include information related to the target patient, and based on the order information, the electronic apparatus 110 may generate at least a part of the one or more pieces of suggested information.

The electronic apparatus 110 provides the acquired one or more pieces of suggested information to the user (202). For example, the contents of the one or more pieces of suggested information may be output on the screen of the user device 120, or a voice instruction message may be output through the speaker of the user device 120, but the scope of the present disclosure is not limited thereto.

Meanwhile, the electronic apparatus 110 may, in response to receiving at least a part of the one or more suggested information from the operator, additionally provide profile information of the operator to the user together with the one or more suggested information. Such a configuration improve the reliability of the user on the task result, and also improve the convenience of task, such as of allowing the operator and the user to communicate directly through contact information included in the profile as needed.

Figure 3:
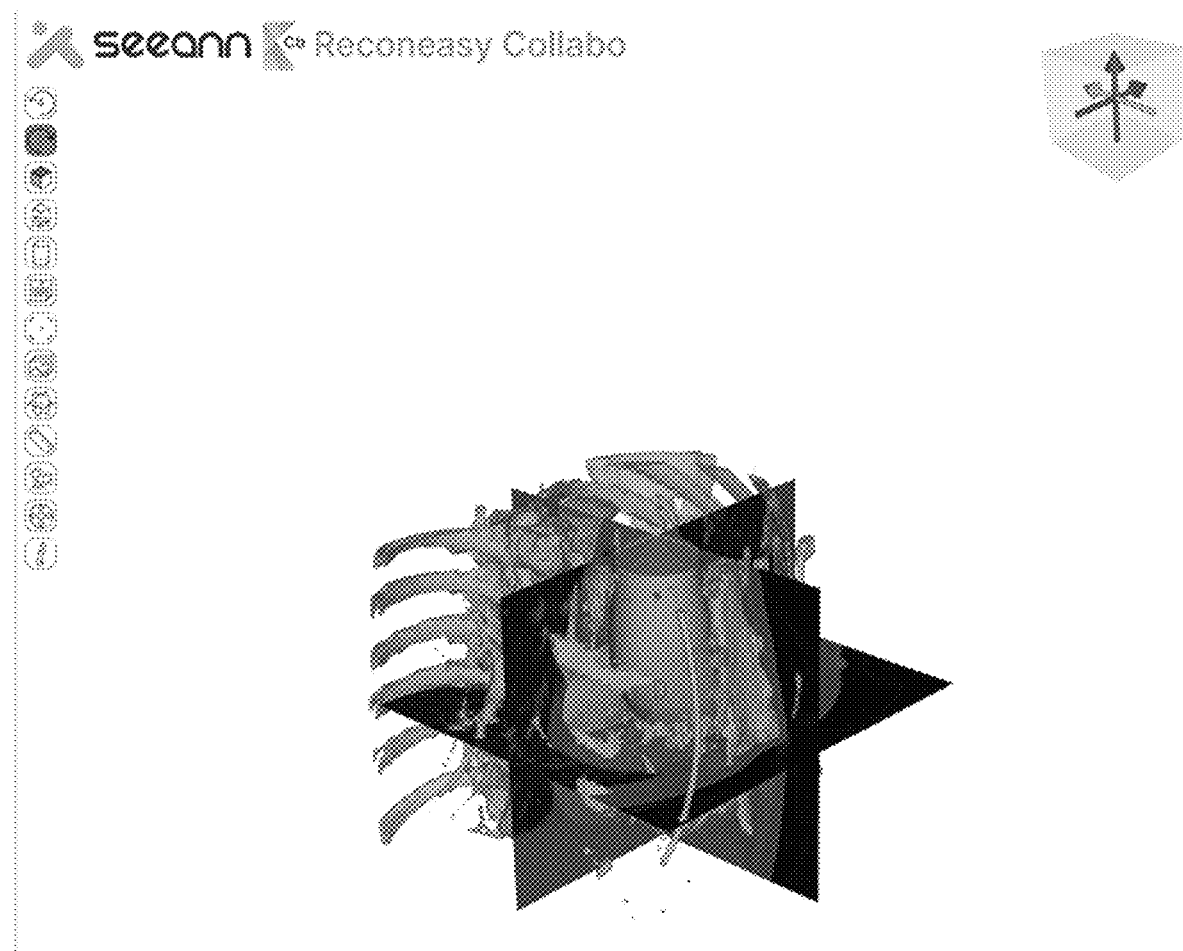
FIG. 3 is a diagram illustrating one or more pieces of suggested information according to an embodiment.

According to an embodiment, the one or more pieces of suggested information may include a 3D modeling image related to at least a body part of the patient based on medical image data of the patient's body, and more specifically, may include providing a 3D modeling image that accurately represents a target body part or organ part of the patient based on a magnetic resonance imager (MRI) and computer tomography (CT) image. As an example, when the medical service is "a provision of a simulation through a patient-customized body organ model," the electronic apparatus 110 may, in consideration of the shape, the state, the disease onset, the deformation absence or presence, and the like of a target body part of a patient, suggest the user information related to 3D modeling of the corresponding body part of the patient based on the corresponding conditions. As another example, when the medical service is "an insertion/replacement surgery of an implant or graft material," the electronic apparatus 110 may, in consideration of the implant or graft material to be inserted, or the structure, the deformation presence/absence, and the degree of deformation of a patient's body part which to receive the surgery, suggest the user information related to 3D modeling of the corresponding body part based on the corresponding conditions. As another example, when the medical service provided by the user is "a production of an orthosis", the electronic apparatus 110 may consider the structure, the deformation presence/absence, and the degree of deformation of a patient's body part which to use the orthosis, suggest the user information related to 3D modeling of the corresponding body part based on the corresponding conditions. As a specific example, the suggested information may include a 3D modeling image of an aortic region of a target patient, as shown in FIG. 3.

Figure 4:
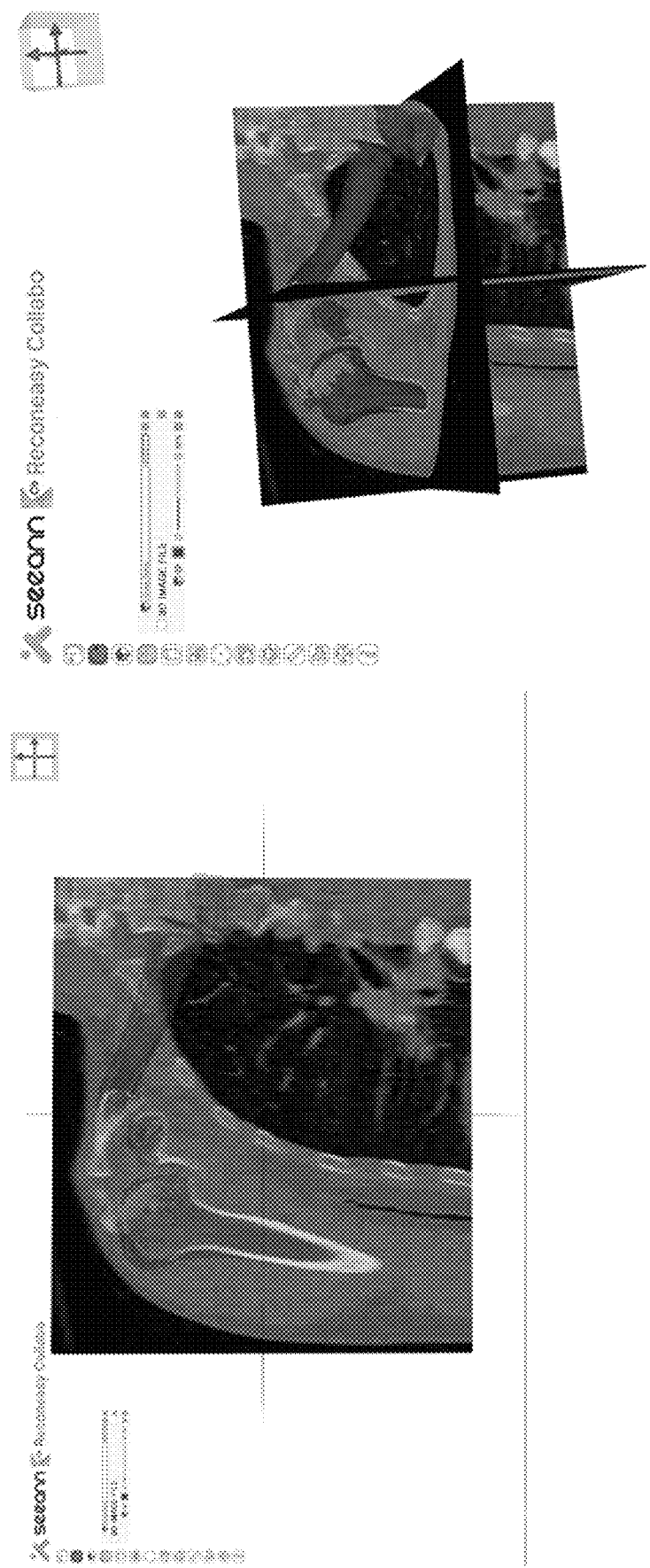
FIG. 4 is a diagram illustrating one or more pieces of suggested information according to an embodiment.
Figure 5:
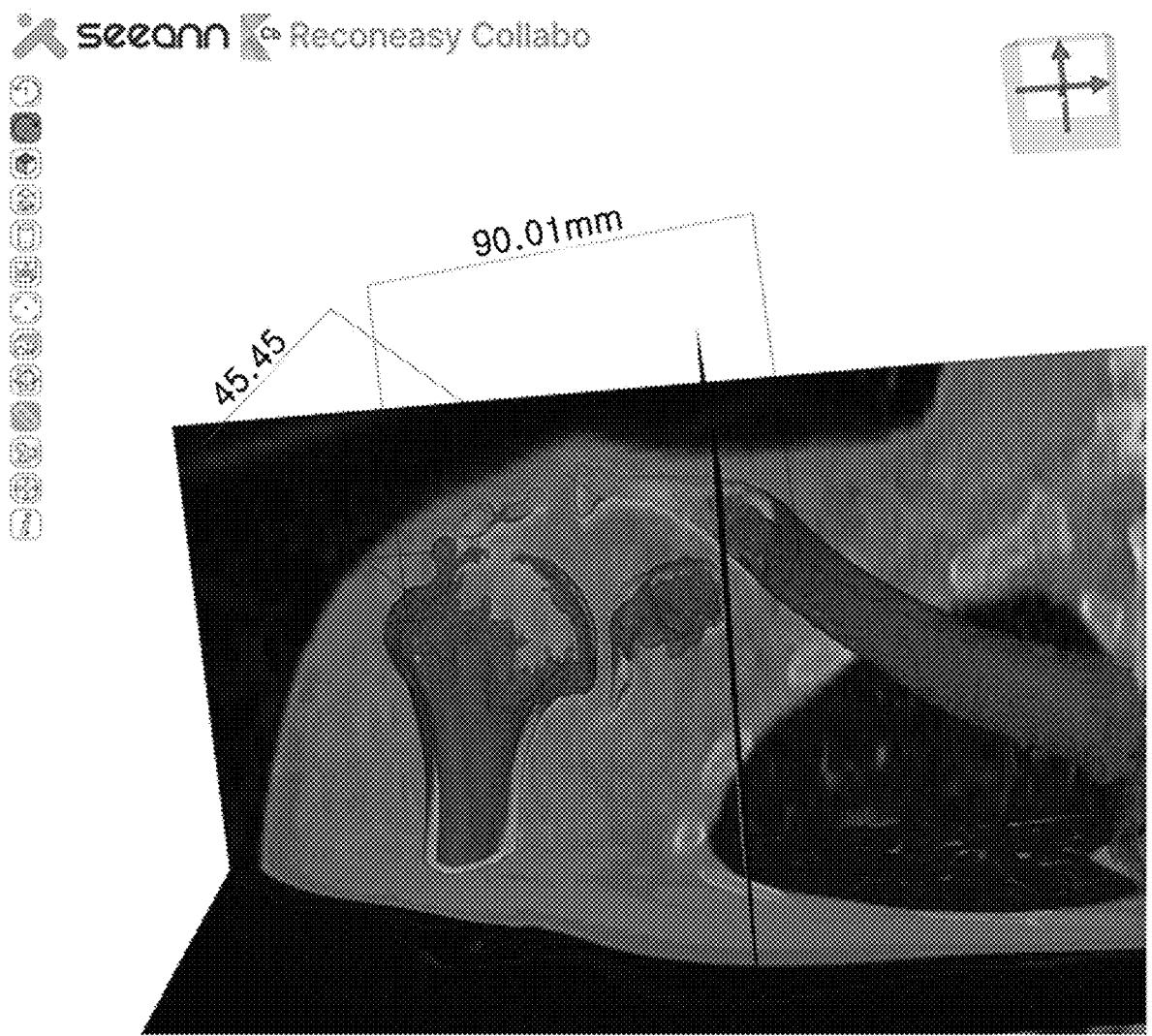
FIG. 5 is a diagram illustrating one or more pieces of suggested information according to an embodiment.
Figure 6:
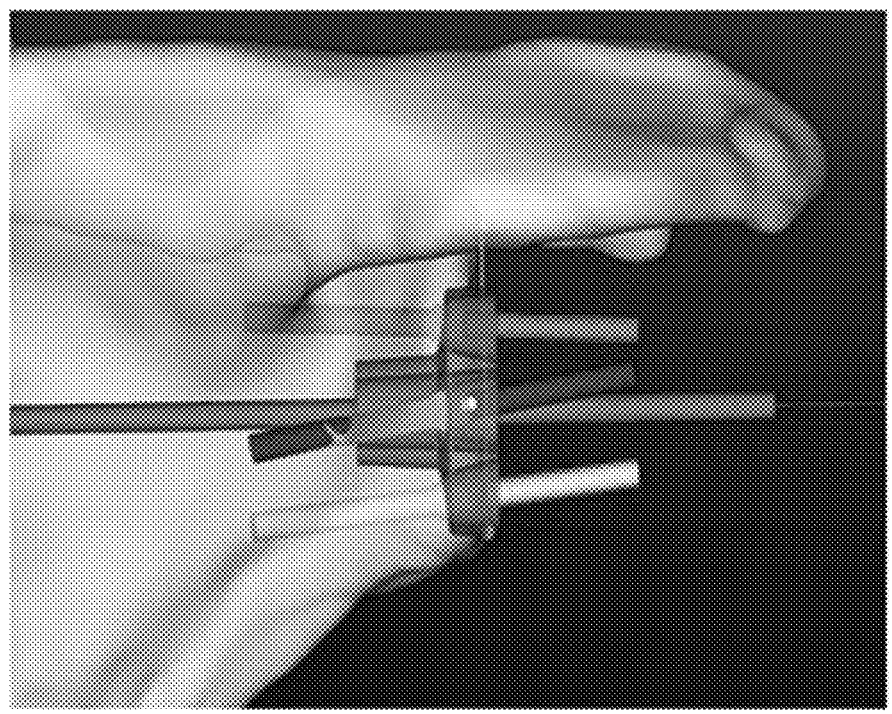
FIG. 6 is a diagram illustrating one or more pieces of suggested information according to an embodiment.

According to an embodiment, the one or more pieces of suggested information may include information for suggesting one or more items selected from a shape, a material, a color, a transparency, a size, a weight, a price, a producing deadline, an application location, an angle, a depth, and a specific operation of producing a patient-customized body model or a patient-customized medical device. Here, visual representation information of the body model or medical device included in the suggested information may include forms, such as point clouds, wire frames, textured frames, or 3D modeling. In the case of a color and a transparency, a patient's body part may be represented in different colors or transparencies for each tissue, and a medical device may be represented in different colors or transparencies for each device that forms the medical device. In the case of a size, size/length information may be provided for the entirety or a selected portion of the corresponding body part or the medical device. Meanwhile, as an example of the suggested information, the electronic apparatus 110 may include information for suggesting one or more items selected from a shape, a material, a color, a transparency, a size, a weight, a price, a production deadline, and a specific operation of producing 3D modeling of a target body model of a patent. More specifically, the suggested information may include a 3D modeling image of a shoulder joint and shoulder skeleton of a patient as shown in FIGS. 4 and 5, while including information about the shape of the shoulder joint and shoulder skeleton as shown in FIG. 4, as well as information about a 3D image in which the transparency may be adjusted at various levels, or including length information of a region of at least a part of the shoulder joint and shoulder skeleton, as shown in FIG. 5. As another example, the electronic apparatus 110 may include information for suggesting one or more items selected from a shape, a material, a color, a transparency, a size, a weight, a price, a production deadline, and a specific operation of producing 3D modeling of an implant or a graft material to be used in an insertion/replacement surgery of the implant or graft material. As another example, the electronic apparatus 100 may suggest, with regard to a surgery guidance for an insertion/replacement surgery of an implant or graft material, and more specifically, a joint replacement surgery implant or surgery guidance, such as a center-pin, a base plate, and a screw; a mandibular replacement surgery guidance for treatment of an oral cancer, such as a mandibular support; or a cutting guidance fora calf bone (fibula) that is to be inserted as a graft material, suggest a user a shape, a material, a manufacturer of commercially available components, a price, and a specific operation of producing the guidance. For example, the suggested information may include a 3D modeling image of a center pin, a base plate, and a screw as a guidance to be applied to a shoulder joint replacement surgery, as shown in FIG. 6, and may include information distinguished by various colors for each component.

As another example, the electronic apparatus 110 may, with regard to an orthosis, suggest a user a shape, a material, a color, a size, a weight, a price and the like of a finger orthosis or a toe orthosis in consideration of the overall patient's physical conditions.

Figure 7:
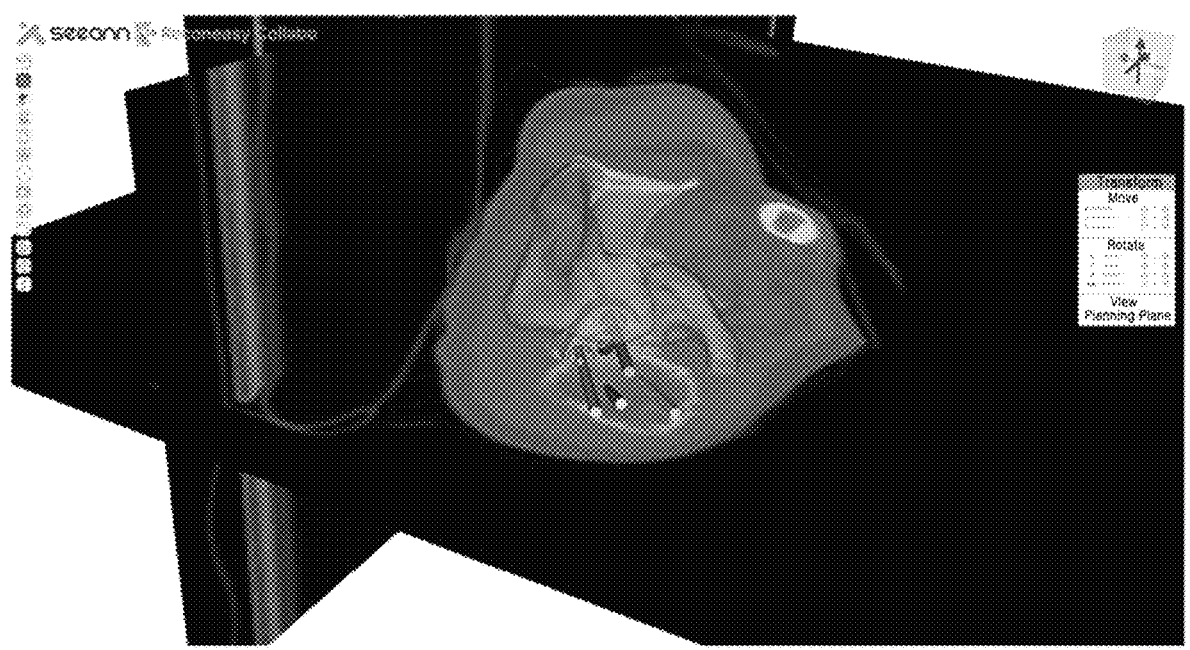
FIG. 7 is a diagram illustrating one or more pieces of suggested information according to an embodiment.

According to an embodiment, the one or more pieces of suggested information may include specific guidance information for a medical service that uses a patient-customized medical device. The suggested information according to one example may include instruction information about specific and detailed methods related to a specific operation or specific action of a medical service, and examples related thereto are illustrated in FIG. 3 (300). For example, the one or more pieces of suggested information may include information for suggesting a patient a structure of a surgery guidance that enables a precise surgery in relation to a replacement surgery of an artificial joint (e.g., a shoulder joint, a knee joint, a hip joint, and the like) and a specific insertion location, an insertion angle, and an insertion depth of the surgery guidance, and more specifically, as shown in FIG. 7, include information for suggesting a structure, an insertion location, an insertion angle, and a depth of a center-pin, a base plate, and a screw serving as a surgery guidance to be applied to a shoulder joint replacement surgery.

Figure 8:
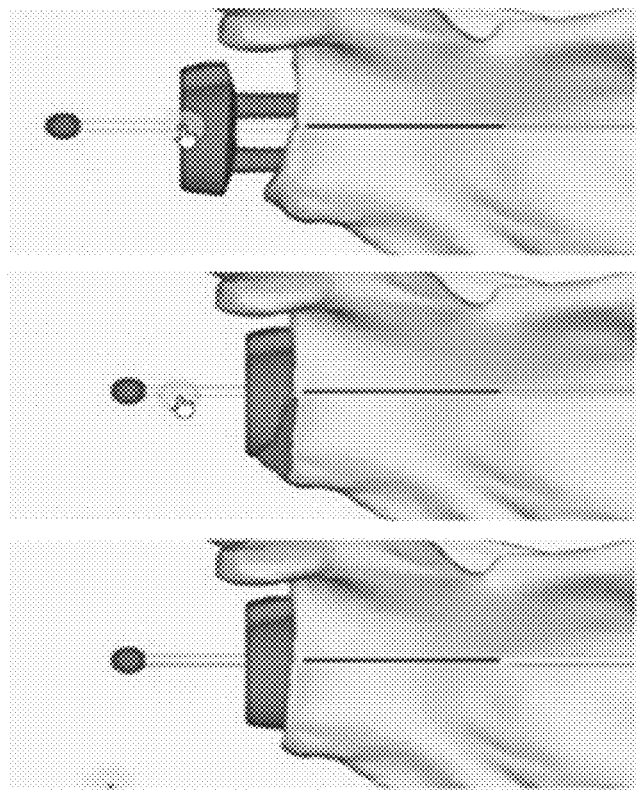
FIG. 8 is a diagram illustrating one or more pieces of suggested information according to an embodiment.

According to an embodiment, the one or more pieces of suggested information may include simulation information about a changes that may occur in the patient's body after application of the patient-customized medical device. As an example, in relation to a replacement surgery of an artificial joint (e.g., a shoulder joint, a knee joint, a hip joint and the like) or a bone (e.g., a lower jaw), the one or more pieces of suggested information may include information for suggesting a changes that may occur in the patient's body after application of a surgery guidance or after insertion of an implant/graft material. More specifically, the one or more pieces of suggested information may include information for suggesting a simulation result of deformation of a body part at an insertion or application location after an insertion of an implant/graft material or an application of a surgery guidance, or information for suggesting a simulation result about the degree of overlap, the radius of movement, or the angle of rotation of the artificial glenoid and the artificial humeral head of the patient after an insertion of a shoulder joint replacement surgery implant. For example, as shown in FIG. 8, the one or more pieces of suggested information may include information of a simulation result about a glenoid deformation after an application of a shoulder joint replacement surgery guidance. However, the degree of overlap (for example, the degree of overlap between the artificial glenoid and the artificial humeral head) between the inserted implant and the body part (bones or other tissues) of the patient in contact with the implant may be represented using technology, such as a color map and the like, or may be represented in a percentage (%) according to the areas and other various methods, but it is not limited thereto.

Figure 9:
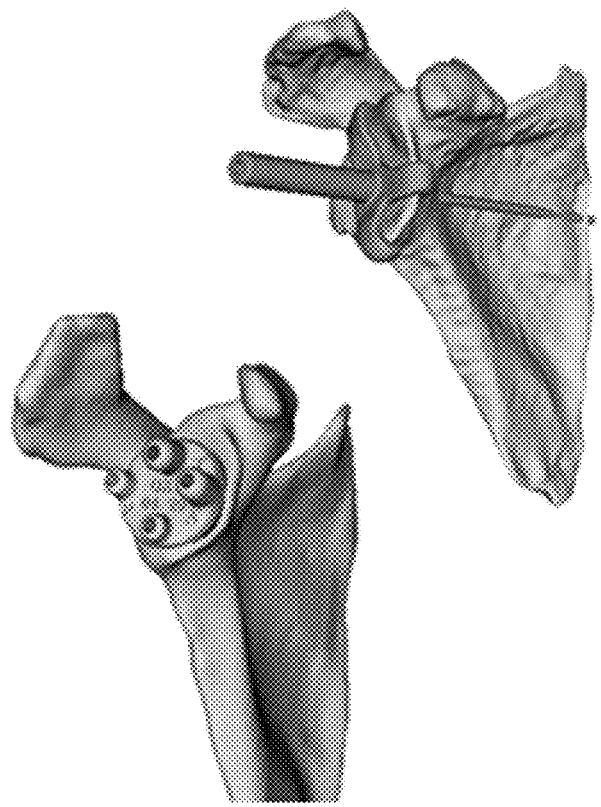
FIG. 9 is a diagram illustrating one or more pieces of suggested information according to an embodiment.

In addition, according to an embodiment, the one or more pieces of suggested information may include information for providing a function of producing an implant or graft material to be inserted into a patient, or a surgery guidance that is applied to an insertion/replacement surgery of the implant or graft material, or may include suggested information about an implant or a surgery guidance semi-automatically produced through 3D modeling. As an example, the one or more pieces of suggested information may include information related to a function (e.g., adjusting the number, the thickness, the angle, the color, and the like) of semi-automatically producing a cylinder for a center-pin or a screw, which is a guidance for a shoulder joint replacement surgery. As another example, the one or more pieces of suggested information may include information related to a function of semi-automatically producing a center-pin, a base plates, and a screw that meet the specifications of each manufacturer. As a more specific example, the one or more pieces of suggested information may include information related to a function (e.g., positioning and shaping of the module) of semi-automatically producing a center-pin, a base plate, and a screw when four points on a glenoid are selected from the patient's body model included in the suggested information. As another example, as shown in FIG. 9, the one or more pieces of suggested information may include suggested information about a shoulder joint replacement surgery guidance module to be applied to a patient and a guidance semi-automatically produced through 3D modeling.

Figure 10:
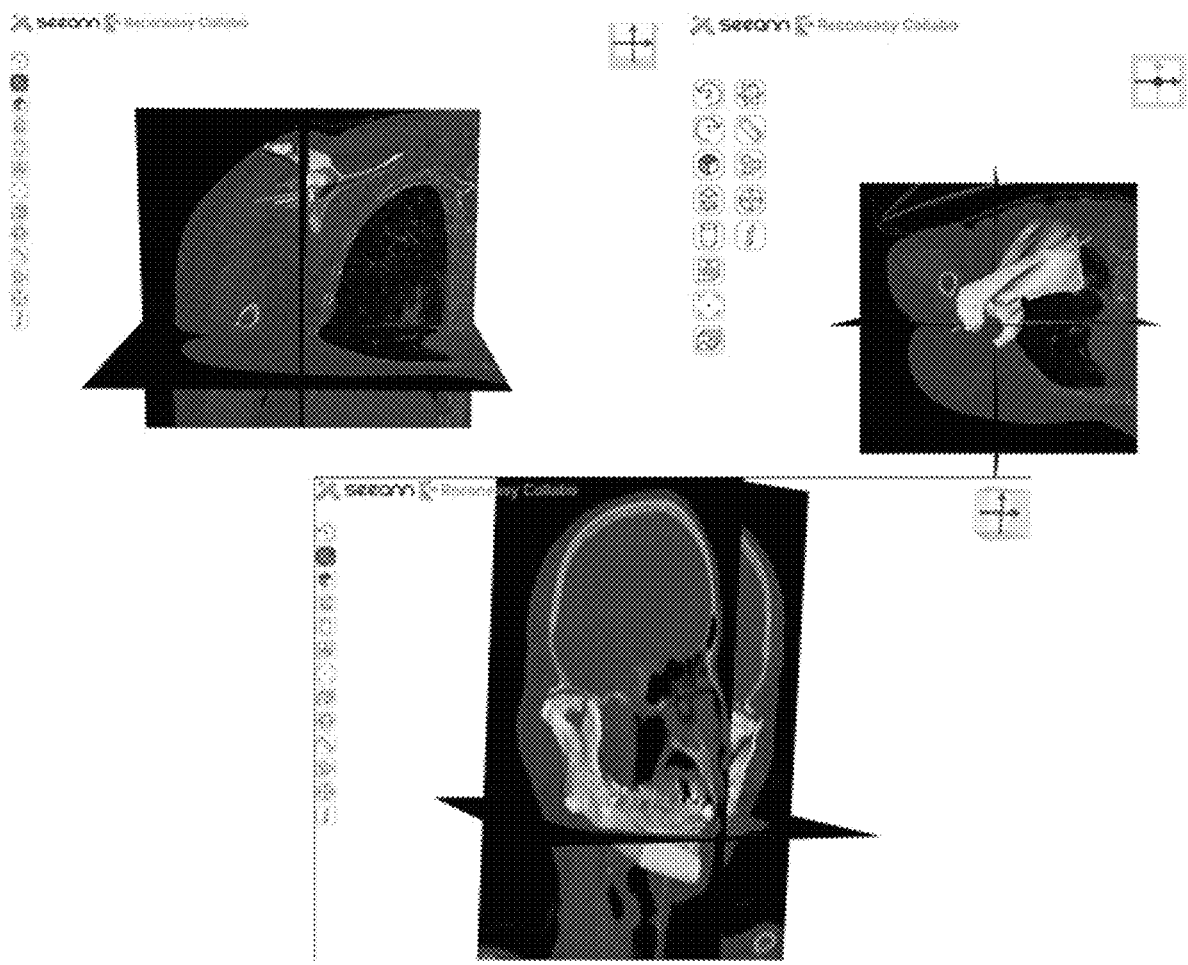
FIG. 10 is a diagram illustrating one or more pieces of suggested information according to an embodiment.
Figure 11:
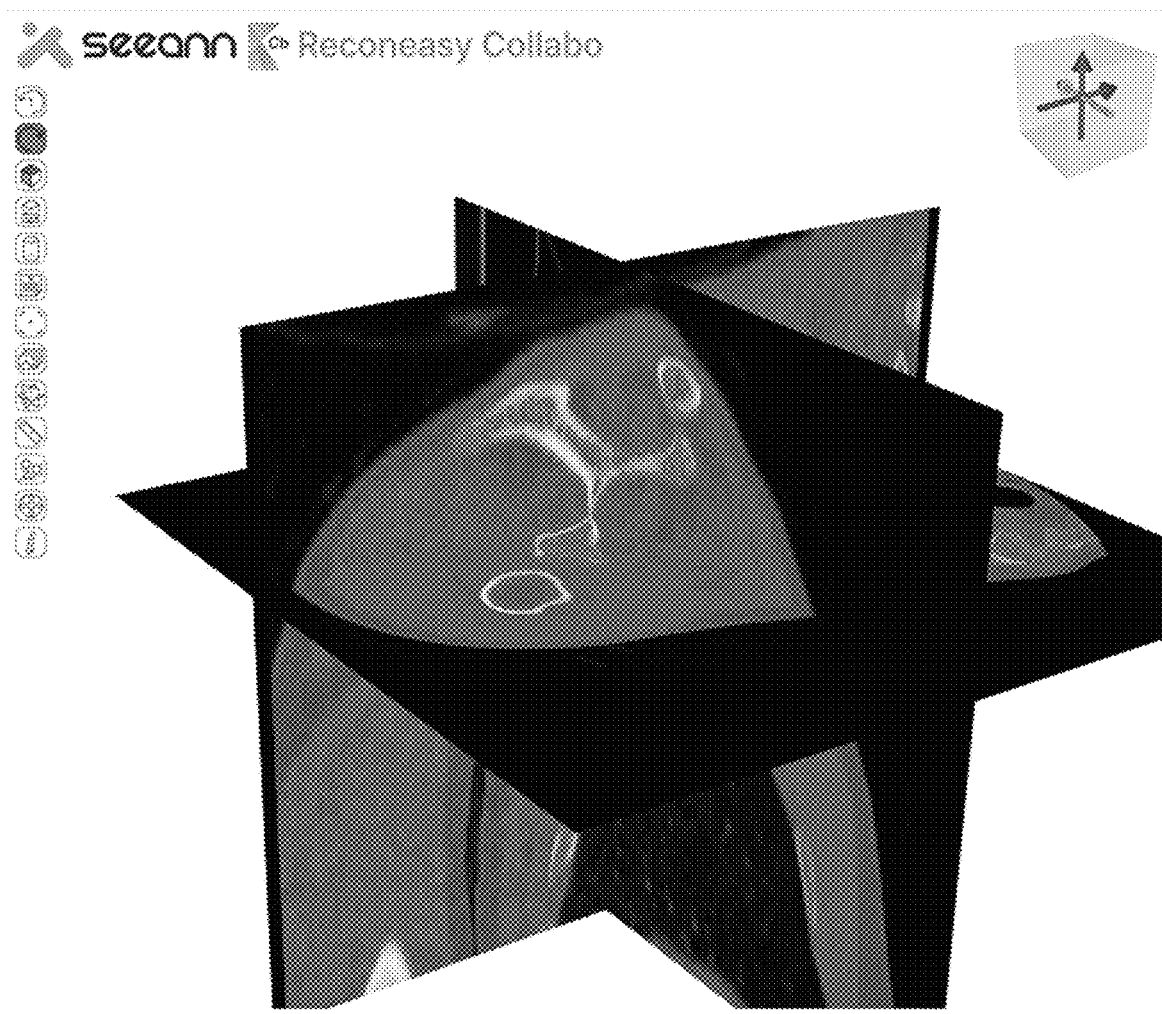
FIG. 11 is a diagram illustrating one or more pieces of suggested information according to an embodiment.

In addition, according to an embodiment, the one or more pieces of suggested information may include, as information for evaluating the quality or suitability of an item used in a medical service prior to a direct medical treatment. In this case, the one or more piece of suggested information may, when the medical service is a provision of a patient-customized body organ model, an insertion/replacement surgery of an implant or graft material, or a production of an orthosis, include medical image data (e.g., an MRI or CT image) of a patient, or information related to the degree of patient-specific matching obtained by overlaying a 3D image of a medical device or a body model included in the suggested information on the medical image data. However, the medical image data may be a digital imaging communication in medicine (DICOM) file, which is standardized medical image information that is currently used in common. For reference, DICOM is a general term for several standards used for digital image representation and communication in medical devices published by the American College of Radiology (ACR) and the National Electrical Manufacturers Association (NEMA). For a specific example, the suggested information may include matching information in which a 3D modeling image of a patient's shoulder joint and shoulder skeleton overlays on a DICOM image as shown in FIG. 10, or matching information in which a 3D modeling image overlays on a CT image as shown in FIG. 11.

Figure 12:
FIG. 12 is a diagram for describing an example related to one or more pieces of suggested information according to an embodiment.
Figure 13:
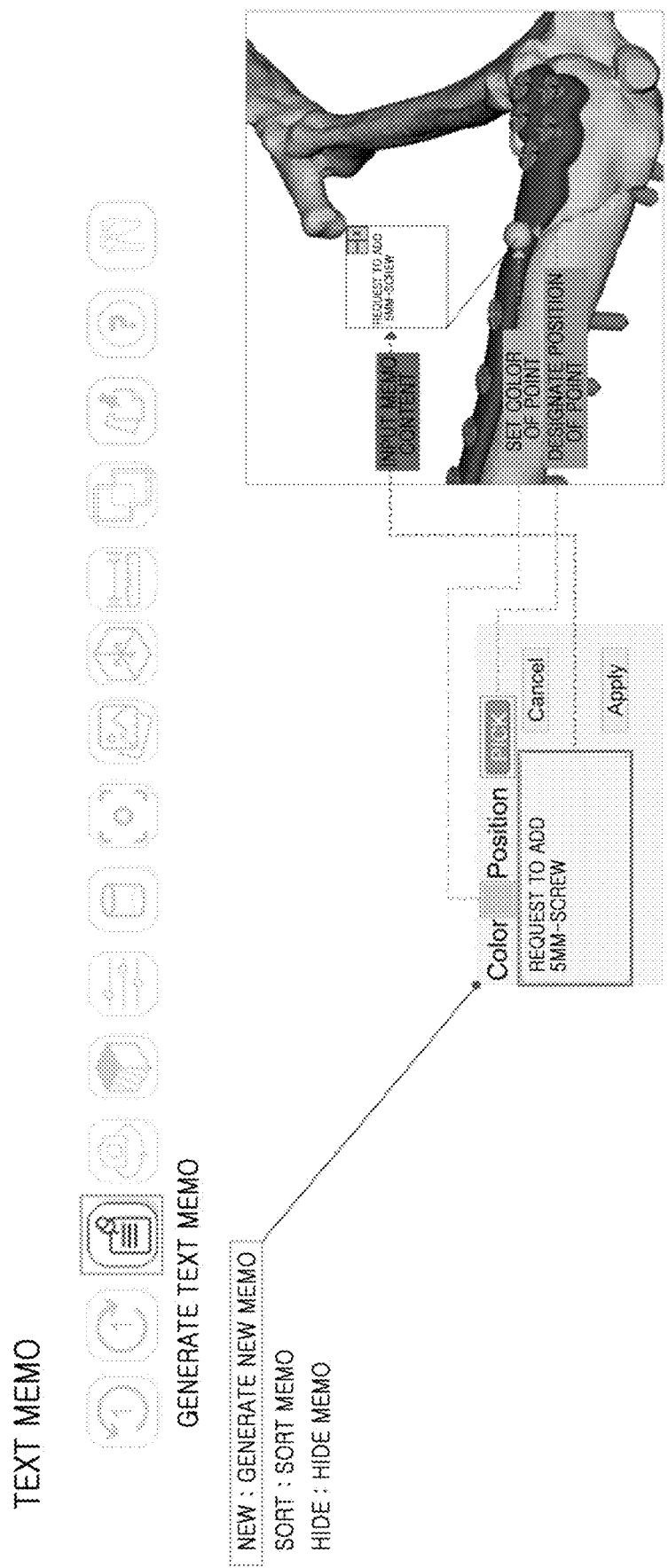
FIG. 13 is a diagram illustrating a modification request according to an embodiment.
Figure 14:
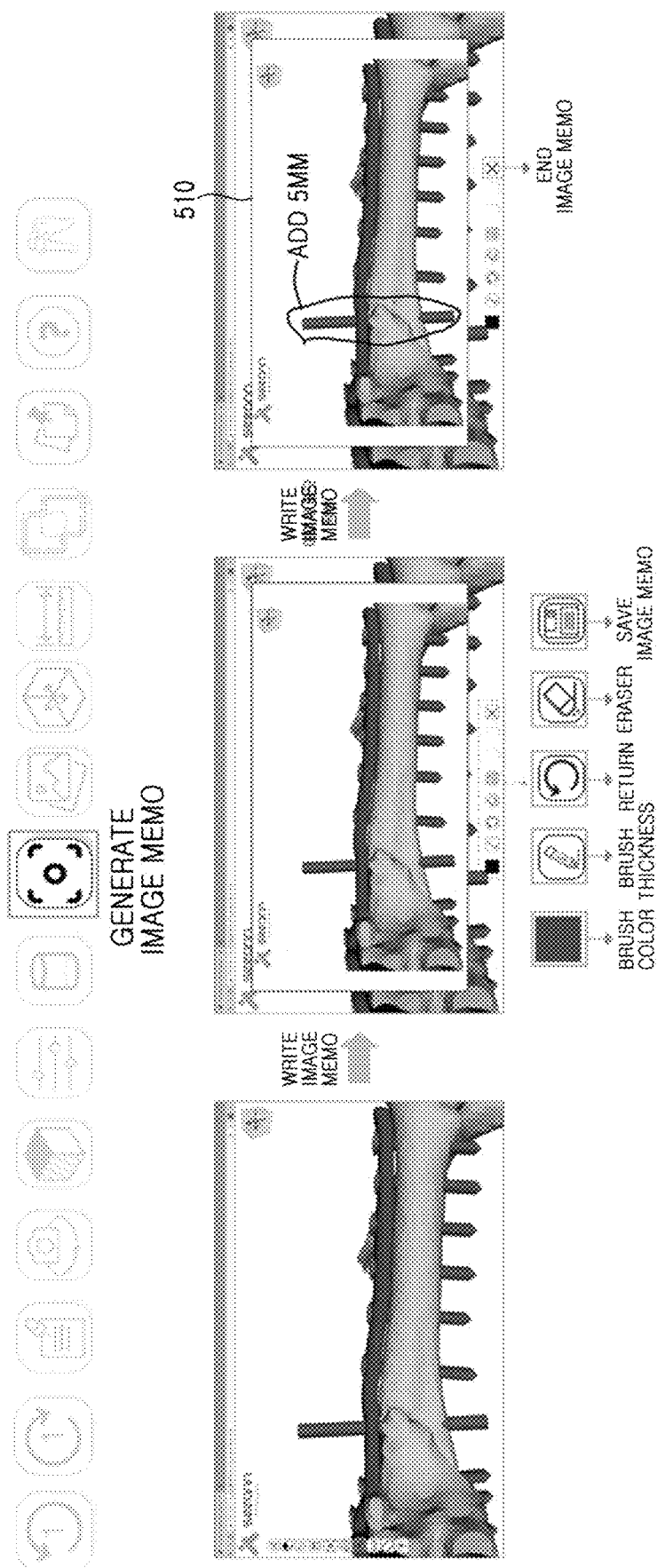
FIG. 14 is a diagram illustrating a modification request according to an embodiment.
Figure 15:
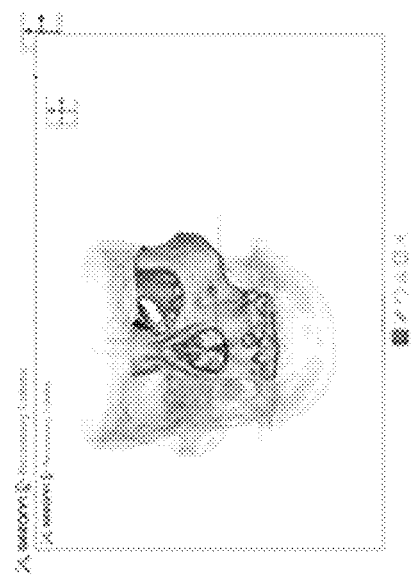
FIG. 15 is a diagram illustrating a specific example related to a process in which a collaborative service is provided according to an embodiment.
Figure 15:
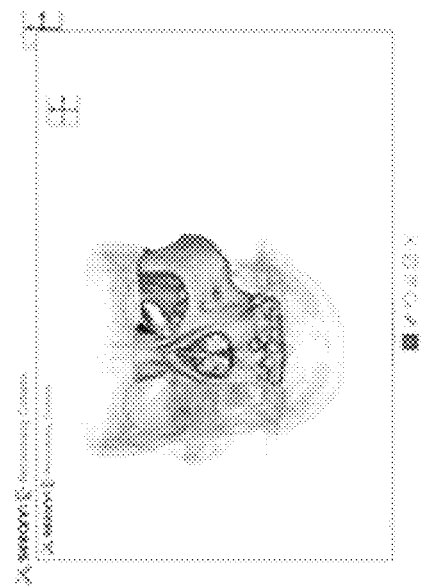
Figure 15:
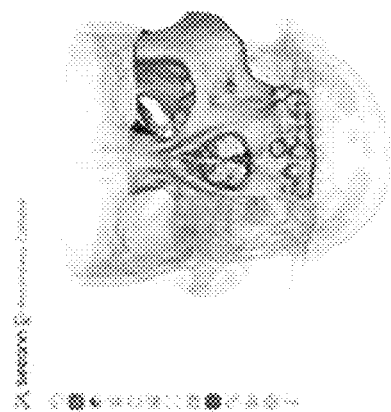
Figure 16:
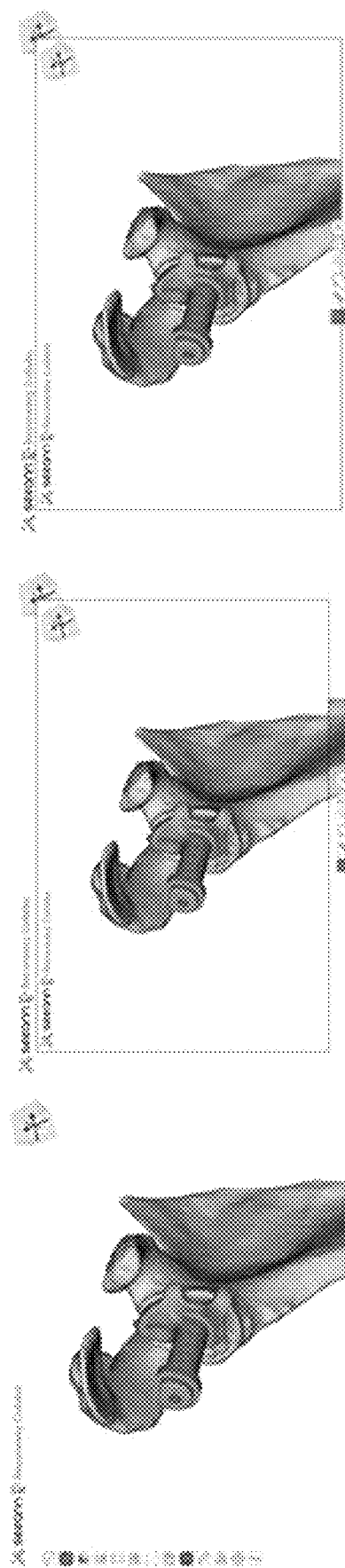
FIG. 16 is a diagram illustrating a specific example related to a process in which a collaborative service is provided according to an embodiment.

In addition, according to an embodiment, the one or more pieces of suggested information may include instruction information about an overall method related to providing a medical service, and an example related thereto is shown in FIG. 12 (400). Referring further to FIG. 12, the one or more pieces of suggested information may include information 410 related to a surgical preparation operation, for instructing to prepare a surgical tool, wear a surgical gown, and prepare an implant or graft material, information 420 related to a surgery start operation, for instructing to anesthetize a patient, disinfect a surgical site, and cut the surgical site, and information 430 related to an insertion operation of the implant or graft material, for informing a specific location to insert the implant or graft material. Additionally, upon receiving a user input regarding the guide for each operation included in the one or more pieces of suggested information, the electronic apparatus 110 may provide further detailed information in response to the user input. For example, detailed information may be provided by clicking on an interface "View More" located on the right side of each guide in FIG. 12.

Furthermore, according to an embodiment, the electronic apparatus 110 may receive one or more pieces of context information related to the provision of a medical service and provide suggested information related to each of the one or more pieces of context information. For example, in relation to the example of FIG. 12, the electronic apparatus 110 may, upon receiving, from the user device 120 and the like, information indicating that the current operation corresponds to a surgery preparation, provide information related thereto as shown in operation 410 of FIG. 12, and upon receiving information indicating that the current operation corresponds to a surgery start, provide information related thereto as shown in operation 420 of FIG. 12, and upon receiving information indicating that the current operation corresponds to an insertion of an implant or graft material, provide information related thereto as shown in operation 430 of FIG. 12.

Meanwhile, an example in which context information is received from the user device 120 has been described, but the scope of the present disclosure is not limited thereto. For example, various embodiments may be present such as context information may be automatically transmitted by a surgical device, or the situation may be automatically determined as a medical service provision screen of a user is identified by the electronic apparatus 110.

The examples described above with reference to FIGS. 3 to 12 are specific examples of the one or more pieces of suggested information according to the present disclosure, but the scope of the present disclosure is not limited thereto. In addition, the one or more pieces of suggested information may include information for providing a timer related to the provision of each medical service and the like, and there may be various examples related to the one or more pieces of suggested information.

Returning to FIG. 2, the user device 120 transmits response information regarding the one or more pieces of suggested information (203). The response information may include various types of information, such as an approval of the suggested information, a rejection of the suggested information, a manipulation of the suggested information, a request for modification of the suggested information, and the like.

According to an embodiment, the response information may include image information acquired by manipulating 3D modeling of a patient-customized body part or 3D modeling of a patient-customized medical device. As an example, the response information may include 3D modeling information that is obtained by shift, zoom-in, zoom-out, rotation, or twist in the XYZ axis direction for all or a part of the 3D modeling. As another example, all or a part of elements constituting the 3D modeling may be grouped, and the response information may include 3D modeling information about the group given a group name, or image information obtained by manipulating the group. When a plurality of elements are grouped into one group, shift, zoom-in/zoom-out, rotation, and the like may be applicable to the entire group as a whole. The 3D modeling image changed as described above may be projected to provide the user with continuous visual feedback.

According to an embodiment, when the response information includes a request for modifying at least a part of the one or more pieces of suggested information, the electronic apparatus 110 initiates a process for modifying the at least a part of the one or more pieces of suggested information (204). A request for modifying each of the one or more pieces of suggested information may be a request for modifying the entire information, or may be a request for modifying only a part of the information. For example, in relation to providing a guidance for a joint replacement surgery, a user may provide information requesting a modification for a group of a plurality of screws included in the suggested information, or may approve or request a modification for individual screws.

According to an embodiment, examples in which response information includes a request for modification related to at least a part of the one or more pieces of suggested information are shown in FIGS. 13 to 16. With further reference to FIGS. 13 to 16, the user may provide an input 510 corresponding to a modification request on the user device 120, thereby requesting a modification of at least a part of the one or more pieces of suggested information. In this regard, the input 510 may include an example of simply marking or clicking the position for which the modification is desired, and also include an example of a text memo explicitly entering a phrase, such as "request to add 5 mm screw" (FIG. 13), or an example of an image memo (FIGS. 14, 15, and 16) extracting a specific image and entering a phrase, such as "add 5 mm" into the image, and alternatively, a modification request including modification details may be performed based on various methods, such as a voice chat and a text chat.

According to an embodiment, the response information may include information about all or a part of a medical device additionally designed by the user in response to the suggested information about the 3D modeling of the patient-customized body part, and more specifically, the response information may include a 3D modeling image of all or a part of a medical device desired to be added by the user, information about a shape, a material, a color, a size, a weight, a price and the like of the medial device, and an additional production request that allows an operator to produce the medical device.

Returning to FIG. 2, in greater detail with regard to initiating a process for modifying at least a part of the one or more pieces of suggested information, the electronic apparatus 110 according to an embodiment may request the operator to modify at least a part of the one or more pieces of suggested information. In this case, the operator requested to modify the at least a part of the one or more pieces of suggested information by the electronic apparatus 110 may be the same as or different from the operator who has transmitted the one or more pieces of suggested information, and whether the operator is the same person or not does not limit the scope of disclosure. For example, in order to increase the task efficiency, the electronic apparatus 110 may request a modification from the operator who has transmitted the one or more pieces of suggested information, but when the operator is absent or it is determined as being inappropriate to request a modification from the operator (e.g., the operator in question has a strong tendency to repeat similar mistakes), the modification may be requested from another operator.

The following description is made in relation that, for convenience of description, the operator requested to modify at least a part of one or more pieces of suggested information is the same person as the operator who has transmitted the one or more pieces of suggested information. However, this is only for convenience of description. The description may be applied even when the operator requested for modification of at least a part of the one or more pieces of suggested information may be different from the operator who has transmitted the one or more pieces of suggested information.

According to an embodiment, in relation to initiating a process for modifying at least a part of one or more pieces of suggested information, the electronic apparatus 110 may provide a function for transmitting and receiving information between a user and an operator. For example, the function for transmitting and receiving information may include one or more of a function of providing a first interface to a user and a function of providing a second interface to an operator, and the electronic apparatus 110 may reflect at least a part of an input of the operator in the first interface in real time, and reflect at least a part of an input of the user in the second interface in real time such that real-time information transmission and reception may be achieved.

As a more specific example, the electronic apparatus 110 may provide the user with details of a real-time modification of the operator or a real-time task screen of the operator, and provide a user device 120 with a function that allows the user to input a voice chat, a text chat, a text memo, an image memo and the like in relation to the real-time modification of the operator such that the user may inform whether the modification is appropriate or may provide specific instructions regarding the modification.

Furthermore, there are other various embodiments that provide a function of transmitting and receiving information between the user and the operator, such as the electronic apparatus 110 allows the user and the operator to perform a task together on a single shared screen, enabling the user to directly delete and change the content of the operator's task.

Regarding a process for modifying at least a part of the one or more pieces of suggested information, the electronic apparatus 110 may provide a user's modification request to the operator device 130 in the same manner as shown in FIGS. 13 to 16. The operator may proceed with a modification based on the received modification request and provide modified suggested information.

Meanwhile, according to embodiments, with regard to the screen displayed on the operator device 130 shown in FIGS. 13 to 16, the screen may be shared with the user, or at least a part of the content input by the operator on the screen may be transmitted to the user device 120 such that transmission and reception of information between the user and the operator is achieved.

Returning to FIG. 2, the electronic apparatus 110 may repeatedly perform at least a part of the operations indicated by reference numerals 201 to 204 as needed. For example, after a process for modification is performed, the electronic apparatus 110 may provide the modified suggested information, and when the user may find another error, the user may transmit additional response information for requesting an additional modification to the electronic apparatus 110, in which case the process for modification may initiate again.

According to an embodiment, the electronic apparatus 110 may group one or more pieces of suggested information and response information corresponding thereto and store the one or more pieces of suggested information and the response information corresponding thereto in a database. Here, the database may be understood as a broad concept that include not only external devices distinct from the electronic apparatus 110, but also internal memories of the electronic apparatus 110, or a separate cloud service and the like.

The electronic apparatus 110 may acquire feedback information related to an operation of acquiring one or more pieces of suggested information based on the information stored in the database. For example, when an implant or graft material is repeatedly requested by one or more users to be inserted slightly higher than the suggested location in connection with a specific surgery, the electronic apparatus 110 may acquire feedback information for suggesting a slightly higher location as the insertion location in the future. With such a process, the process associated with acquiring one or more pieces of suggested information may be gradually improved.

Meanwhile, according to embodiments, the acquisition of feedback information may be achieved based on a machine learning algorithm. For example, as one or more parameters included in a neural network model for generating suggested information are learned based on information stored in the database, the accuracy of generating suggested information may be gradually improved.

According to an embodiment, the electronic apparatus 110 may acquire information about a result of a medical services provided from a user and the like. The information about the result of providing the medical service may include evaluation information related to the provided medical service. Alternatively, the electronic apparatus 110 may evaluate the provided medical service based on the information about the result of providing the medical service. In this regard, the evaluation of a medical service may be performed based on indicators, such as the objective quality of the medical service, the patient's subjective satisfaction with the medical service, and the efficiency of the medical service (in terms of cost, time and the like), but in the present disclosure, the scope of the evaluation is not limited thereto. In this regard, as an example, the electronic apparatus 110 may acquire a computed tomography (CT) image related to the provision of a medical service and evaluate the objective quality of the medical service based on the acquired CT image.

According to an embodiment, the electronic apparatus 110 may acquire feedback information related to an operation of acquiring the one or more pieces of suggested information based on the result information. For example, in relation to a particular surgery, when an implant or graft material is inserted according to a suggested location, but the surgery is not completely successful, a suggestion process may be improved such that the suggested location is be slightly adjusted in the future.

According to an embodiment, the acquisition of feedback information based on the result information may be achieved based on a machine learning algorithm.

According to an embodiment, the electronic apparatus 110 may, in addition to the one or more pieces of suggested information and the response information corresponding thereto, further group the result information corresponding thereto and store the grouped information in the database, and may further group the feedback information and store the grouped information in the database, that is, the combination of pieces of information grouped and stored in the database may be determined in various ways.

Figure 17:
FIG. 17 is a diagram illustrating a specific example related to the process of providing a collaborative service according to an embodiment.

FIG. 17 is a diagram illustrating a specific example related to the process of providing a medical service according to an embodiment.

Referring to FIG. 17 (700), the electronic apparatus 110 according to an embodiment may be requested to produce an item used in the medical field (Order in FIG. 17). This may be an example of a request for provision of a medical service.

The electronic apparatus 110 requested to produce the item may acquire one or more pieces of suggested information related to the item through 3D modeling and 3D design of the item (3D Modeling and 3D Design in FIG. 17). The generated information may suggest various types of information including not only the shape of the item, but also one or more of the material, the color, the size, the weight, and the price of the item, and furthermore, there are other various embodiments such as suggesting one or more of a specific location, an angle, and a depth for inserting the item in relation to a specific medical practice.

Meanwhile, an entity performing the 3D modeling and 3D design may be the electronic apparatus 110 or an operator using the operator device 130, and at least a part of the operations may be performed by various entities.

The electronic apparatus 110 may receive confirmation of the appropriateness of the one or more pieces of suggested information through opinion sharing (Communication—Confirm in FIG. 17). More specifically, the electronic apparatus 110 may provide one or more pieces of suggested information to a user and receive response information regarding the one or more pieces of suggested information. Upon receiving a modification request for at least a part of the one or more pieces of suggested information as the response information, the electronic apparatus 110 may initiate a process for modifying the at least a part of the one or more pieces of suggested information. In this regard, the user who receives the suggested information may be a person who has requested the production of the item but not limited thereto. For example, when the production of an item is requested by an ordinary consumer, a medical professional or specialist with more specialized knowledge related to the appropriateness of the item may serve as the user to determine whether the one or more pieces of suggested information are appropriate.

When the confirmation of the one or more pieces of suggested information is completed, the electronic apparatus 110 may produce the item according to the one or more pieces of suggested information (3D Printing in FIG. 17) and deliver the produced item (Delivery in FIG. 17).

Figure 18:
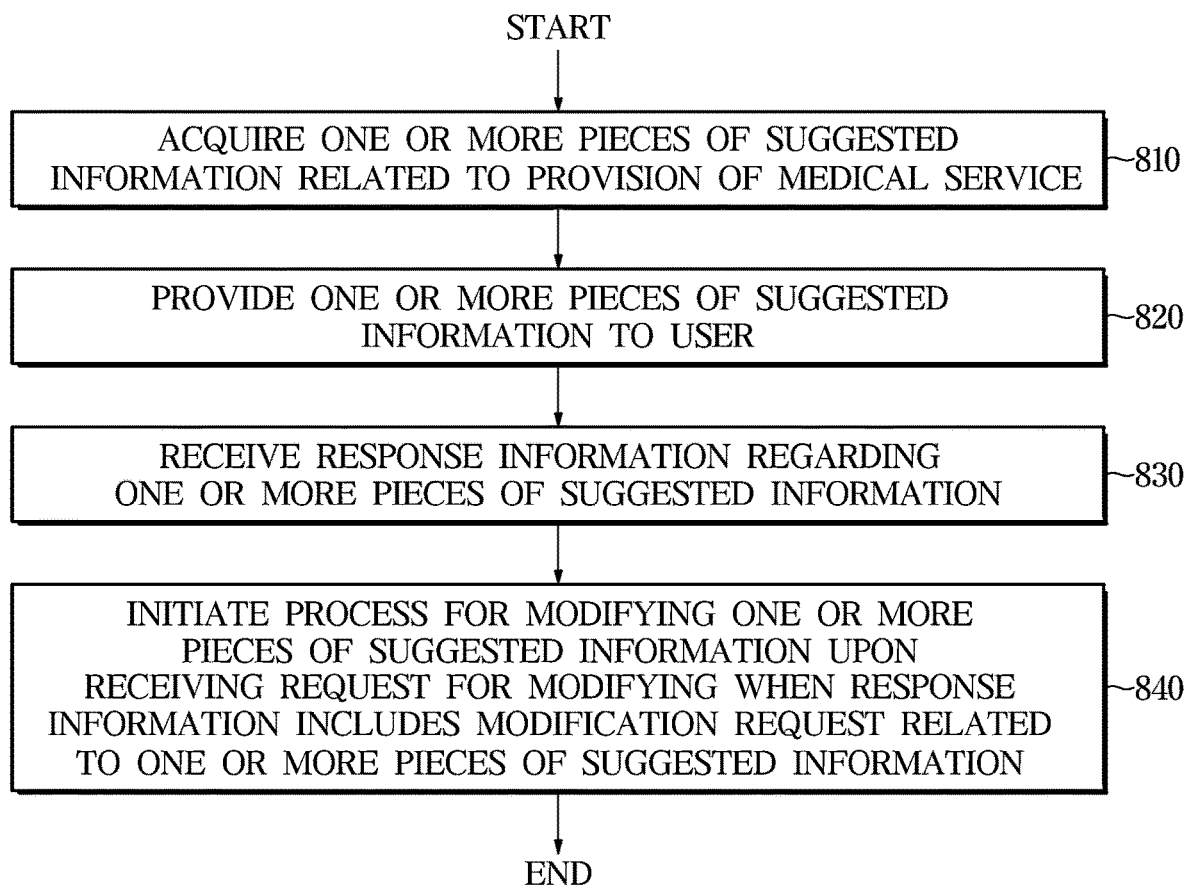
FIG. 18 is an operation flowchart showing a method for an electronic apparatus to perform an operation of providing a collaborative service according to an embodiment.

FIG. 18 is an operation flowchart showing a method for an electronic apparatus to perform an operation of providing a collaborative service according to an embodiment.

Referring to FIG. 18, the electronic apparatus 110 according to an embodiment acquires one or more pieces of suggested information related to provision of a medical service (810). The one or more pieces of suggested information may include, for example, information for suggesting specific location information related to a surgery.

The electronic apparatus 110 provides the one or more pieces of suggested information to a user (820). The electronic apparatus 110 receives response information regarding the one or more pieces of suggested information from the user (830). The response information may include various types of information, such as an approval of the suggested information, a rejection of the suggested information, and a request for modification of the suggested information.

When the response information includes a modification request related to at least a part of the one or more pieces of suggested information, the electronic apparatus 110 initiates a process for modifying the at least a part of the one or more pieces of suggested information (840). According to an embodiment, in relation to the initiating of the process for modifying the at least a part of the one or more pieces of suggested information, the electronic apparatus 110 may provide a function for transmitting and receiving information between a user and an operator.

According to an embodiment, the electronic apparatus 110 may acquire information about a result of providing the medical service from the user and the like, and based on the information, improve a series of processes related to providing the medical service.

Figure 19:
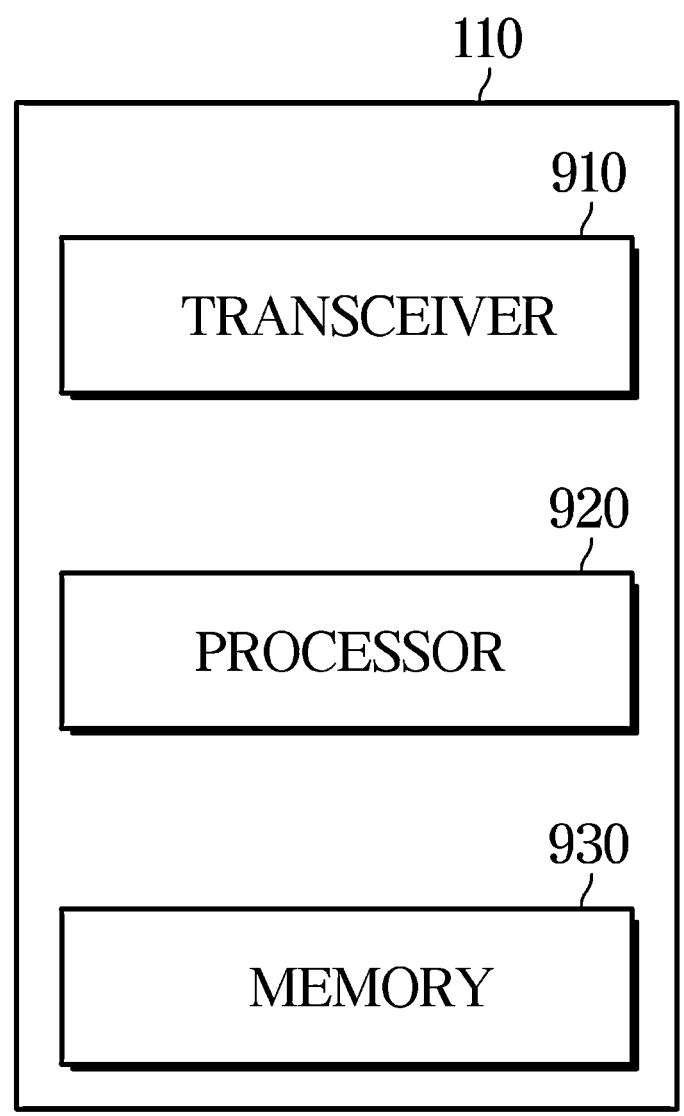
FIG. 19 is a block diagram illustrating a configuration of an electronic apparatus for performing an operation of providing a collaborative service according to an embodiment.

FIG. 19 is a block diagram illustrating a configuration of an electronic apparatus for performing an operation of providing a medical service according to an embodiment.

Referring to FIG. 19, the electronic apparatus 110 includes a transceiver 910, a processor 920, and a memory 930. The electronic apparatus 110 may be connected to the user device 120 and other external devices through the transceiver 910 and exchange data with the user device 120 and other external devices.

The processor 920 may include at least one device described above with reference to FIGS. 1 to 18 or may perform at least one method described above with reference to FIGS. 1 to 18. The memory 930 may store information for performing at least one method described above with reference to FIGS. 1 to 18. The memory 930 may be a volatile memory or a non-volatile memory.

The processor 920 may execute programs and control the electronic apparatus 110 for providing information. A program code executed by the processor 920 may be stored in the memory 930.

In addition, the electronic apparatus 110 according to an embodiment may further include an interface that may provide information to the user.

Meanwhile, exemplary embodiments of the present invention are shown by way of example in the specification and the drawings and specific terms are used, but they are merely intended to aid in the explanation and understanding of the technical spirit of the present invention rather than limiting the scope of the present invention. Those of ordinary skill in the technical field to which the present invention pertains should be able to appreciate that various modifications and alterations may be made without departing from the technical spirit or scope of the present invention.

The electronic apparatus or the terminal according to the above embodiments may include a processor, a memory for storing and executing program data, a permanent storage such as a disk drive, and a user interface device, such as a communication port for communicating with an external device, a touch panel, a key, a button, and the like. Methods implemented with software modules or algorithms may be stored on a computer readable recording medium as computer readable codes or program instructions executable on the processor. Here, the computer-readable recording media include a magnetic storage medium (e.g., a read-only memory (ROM), a random-access memory (RAM), a floppy disk, a hard disk, and the like), an optical readable medium (e.g., a compact disk (CD)-ROM, a digital versatile disk (DVD), etc.) and other recording media. The computer-readable recording medium may be distributed over computer systems connected through a network so that computer readable codes may be stored and executed in a distributed manner. The medium may be readable by a computer, stored in a memory, and executable in a processor.

The embodiments may be represented by functional block configurations and various processing steps. These functional blocks may be implemented with any number of hardware and/or software configurations that perform particular functions. For example, the embodiments may adopt integrated circuit configurations such as memory, processing, logic, look-up tables, etc., which may perform various functions by control of one or more microprocessors or by other control devices. Similar to the way in which components may be implemented in software programming or software components, the present embodiments may be implemented in a variety of ways, including C, C++, Java, an assembler, python, and the like. Functional aspects may be implemented with algorithms running on one or more processors. In addition, the present embodiment may employ conventional techniques for electronic environment setting, signal processing, and/or data processing. Terms such as "mechanism", "element", "means", "configuration" may be used broadly and are not limited to mechanical and physical configurations. The term may include the meaning of a series of routines of software in conjunction with a processor or the like.

As is apparent from the above, the present disclosure is implemented to provide a collaborative service between an operator and a user in a three dimensional (3D) modeling task for designing or producing a patient-customized body model or medical device in relation to provision of a medical service, thereby providing a patient-customized body model or medical device that accurately reflects user requirements and thus preventing incorrect or inadequate medical services from being provided.

In addition, the collaborative service according to the present disclosure enables exchange of detailed feedback regarding the results of 3D modeling while enhancing the convenience of feedback exchange.

The effects of the present invention are not limited to those described above, and other effects not described above is clearly understood by those skilled in the art from the above detailed description.

The above-described embodiments are merely examples and other embodiments may be implemented within the scope of the claims described below.

What is claimed is:

1. A method of providing a collaborative service between an operator and a user for design of a patient-customized body model or a patient-customized medical device in an electronic apparatus, the method comprising:
   acquiring a first three-dimensional (3D) modeling image of a body part of a target patient;
   acquiring a second 3D modeling image of a patient-customized medical device;
   overlaying the second 3D modeling image on the first 3D modeling image;
   acquiring matching information by calculating a degree of matching of the body part and the patient-customized medical device, based on the overlayed images;
   acquiring guidance information that is specific guidance including structure, insertion position, angle, and depth for applying the patient-customized medical device to the body part;
   acquiring simulation information that is a simulation result regarding a change that occurs in the body part after the patient-customized medical device is applied to the body part;
   providing the overlayed images, along with suggested information, which includes the matching information, the guidance information, and simulation information, to the user;
   receiving a modification request related to the patient-customized medical device and the guidance information from the user; and
   initiating a process for modifying the patient-customized medical device or the guidance information, wherein the initiating comprises:
providing a function for transmitting and receiving information between the user and the operator,
wherein the function includes at least one of a function for providing a first interface to the user and a function for providing a second interface to the operator, and the electronic apparatus reflects at least a part of an input of the operator in the first interface in real time and reflects at least a part of an input of the user in the second interface in real time;
acquiring feedback information from the operator, in relation with the modification request; and
performing a machine learning based on the feedback information for one or more parameters included in a neural network model for generating the suggested information in real time.

2. The method of claim 1, wherein the suggested information further includes information for providing 3D modeling production function for the patient-customized medical device in a collaborative service between an operator and the user.

3. The method of claim 1, wherein the modification request comprises:
3D modeling information obtained by manipulating shifting, zooming-in, zooming-out, rotating, or twisting on at least a part of the first and second 3D modeling images, on XYZ axes; or
3D modeling information of all or some of groups of 3D modeling elements included in the first and second 3D modeling images, or image information obtained by manipulating the first and second 3D modeling images about all or some of groups of 3D modeling elements included in the first and second 3D modeling images.

4. The method of claim 1, wherein the modification request comprises: a voice chat, a text chat, a text memo, or an image memo that requests modification of at least a part of suggested information of the patient-customized medical device or the guidance information, or content of at least a part of the patient-customized medical device or the guidance information, that is directly deleted or changed by the user.

5. The method of claim 1, further comprising:
grouping one or more pieces of the suggested information and information included in the modification request; and
storing the grouped information, in a database.

6. The method of claim 1, further comprising:
acquiring result information of providing a medical service using the patient-customized medical device; and
acquiring feedback information, in relation with the modification request, based on the result information.

7. The method of claim 1, wherein the patient-customized medical device includes an implant, a graft material, a surgery guidance, or an orthosis, and
the suggested information includes information for suggesting one or more of: a shape, a material, a color, a transparency, a size, a weight, a price, a manufacturing deadline, an application location, an angle, a depth, and a specific producing operation of 3D modeling of the implant, the graft material, the surgery guidance, or the orthosis.

8. A non-transitory computer-readable recording medium on which a program for executing the method of claim 1 is recorded.

9. An electronic apparatus for providing a collaborative service between an operator and a user for design of a patient-customized body model or a patient-customized medical device, the electronic apparatus comprising a transceiver, a memory in which instructions are stored, and a processor,
wherein the processor is configured to, in connection with the transceiver and the memory:
acquire a first three-dimensional (3D) modeling image of a body part of a target patient;
acquire a second 3D modeling image of a patient-customized medical device;
overlay the second 3D modeling image on the first 3D modeling image;
acquire matching information by calculating a degree of matching of the body part and the patient-customized medical device, based on the overlayed images;
acquire guidance information that is specific guidance including structure, insertion position, angle, and depth for applying the patient-customized medical device to the body part;
acquire simulation information that is a simulation result regarding a change that occurs in the body part after the patient-customized medical device is applied to the body part;
provide the overlayed images, along with suggested information, which includes the matching information, the guidance information, and simulation information, to the user;
receive a modification request related to the patient-customized medical device and the guidance information from the user; and
initiate a process for modifying the patient-customized medical device or the guidance information, and
wherein the processor is further configured to:
provide a function for transmitting and receiving information between the user and the operator,
wherein the function includes at least one of a function for providing a first interface to the user and a function for providing a second interface to the operator, and the electronic apparatus reflects at least a part of an input of the operator in the first interface in real time and reflects at least a part of an input of the user in the second interface in real time;
acquire feedback information from the operator, in relation with the modification request; and
perform a machine learning based on the feedback information for one or more parameters included in a neural network model for generating the suggested information in real time.

* * * * *